United States Patent
Kopperschmidt

(10) Patent No.: US 12,029,528 B2
(45) Date of Patent: Jul. 9, 2024

(54) APPARATUS AND METHOD FOR DISINFECTION

(71) Applicant: FRESENIUS MEDICAL CARE DEUTSCHLAND GMBH, Bad Homburg (DE)

(72) Inventor: Pascal Kopperschmidt, Ditttelbrunn (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 927 days.

(21) Appl. No.: 16/626,900

(22) PCT Filed: Jun. 25, 2018

(86) PCT No.: PCT/EP2018/066860
§ 371 (c)(1),
(2) Date: Dec. 27, 2019

(87) PCT Pub. No.: WO2019/002161
PCT Pub. Date: Jan. 3, 2019

(65) Prior Publication Data
US 2020/0315458 A1 Oct. 8, 2020

(30) Foreign Application Priority Data
Jun. 30, 2017 (DE) .................... 10 2017 114 735.7

(51) Int. Cl.
*A61B 5/00* (2006.01)
*A61K 49/00* (2006.01)
(Continued)

(52) U.S. Cl.
CPC .......... *A61B 5/0071* (2013.01); *A61B 5/4848* (2013.01); *A61K 49/0039* (2013.01);
(Continued)

(58) Field of Classification Search
CPC ................ A61B 5/0071; A61B 5/4848; A61K 49/0039; A61L 2/0088; A61L 2/28;
(Continued)

(56) References Cited

U.S. PATENT DOCUMENTS 5,900,067 A * 5/1999 Jones ................. G01N 21/6447
252/301.16
6,524,390 B1 * 2/2003 Jones ..................... C09K 11/06
134/1
(Continued)

FOREIGN PATENT DOCUMENTS

DE 202007017612 3/2008
DE 19655227 8/2009
(Continued)

*Primary Examiner* — Regina M Yoo
(74) *Attorney, Agent, or Firm* — Jacobson Holman PLLC

(57) ABSTRACT

The present invention relates to a method of disinfecting a region, in particular a skin region of a patient, wherein the method comprises the following steps: a) Application of an optically effective substance to the region; and b) Application of a disinfectant to the region, wherein the optically effective substance and the disinfectant are configured such that the optically effective substance is removed by the disinfectant or its optical properties are changed by the disinfectant.

6 Claims, 1 Drawing Sheet

(51) Int. Cl.
*A61L 2/00* (2006.01)
*A61L 2/28* (2006.01)
*A61M 1/16* (2006.01)

(52) U.S. Cl.
CPC .............. *A61L 2/0088* (2013.01); *A61L 2/28* (2013.01); *A61M 1/169* (2013.01); *A61L 2202/15* (2013.01); *A61M 2205/3313* (2013.01)

(58) Field of Classification Search
CPC .............. A61L 2202/15; A61M 1/169; A61M 2205/3313; A61M 1/14; A61M 1/3653; G01N 21/64; A01N 25/00; G08B 21/245
See application file for complete search history.

(56) References Cited

U.S. PATENT DOCUMENTS

| | | | | |
|---|---|---|---|---|
| 6,706,855 | B1* | 3/2004 | Collins | A01N 33/12 428/917 |
| 6,814,816 | B2* | 11/2004 | Achar | A61K 8/49 510/130 |
| 10,613,030 | B2* | 4/2020 | Llamido | A61L 2/24 |
| 2003/0164456 | A1* | 9/2003 | Petrich | G01N 21/6486 250/458.1 |
| 2004/0065350 | A1* | 4/2004 | Achar | A61K 8/4973 436/2 |
| 2005/0090414 | A1* | 4/2005 | Rich | A61K 8/0241 510/136 |
| 2005/0233919 | A1* | 10/2005 | Rich | A61K 8/0241 510/136 |
| 2006/0264346 | A1* | 11/2006 | Sullivan | A61Q 19/10 510/137 |
| 2010/0134296 | A1* | 6/2010 | Hwang | G08B 21/245 340/573.1 |
| 2010/0240600 | A1* | 9/2010 | Shimamoto | A61K 9/06 514/23 |
| 2012/0085931 | A1* | 4/2012 | Burns | C08K 5/0091 564/292 |
| 2012/0214879 | A1* | 8/2012 | Arndt | G01J 1/58 514/724 |
| 2013/0108555 | A1* | 5/2013 | Lary, Jr. | A23L 3/3508 252/301.16 |
| 2014/0327545 | A1* | 11/2014 | Bolling | G08B 21/245 340/573.1 |
| 2018/0214588 | A1* | 8/2018 | Casares | A61L 2/202 |
| 2019/0298866 | A1* | 10/2019 | Majdali | A61L 2/18 |

FOREIGN PATENT DOCUMENTS

| | | |
|---|---|---|
| EP | 2 140 886 | 1/2010 |
| EP | 2 620 165 | 7/2013 |
| WO | WO2007/051141 | 5/2007 |
| WO | WO2008/088424 | 7/2008 |
| WO | WO2011/156913 | 12/2011 |
| WO | WO2014/182591 | 11/2014 |
| WO | WO2017/053055 | 3/2017 |

\* cited by examiner

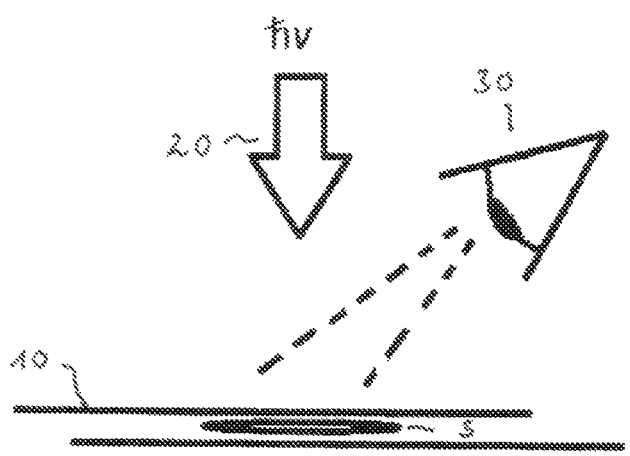

APPARATUS AND METHOD FOR DISINFECTION

The present invention relates to a method and to an apparatus for disinfecting a region, in particular an area of skin of a patient.

It is necessary as part of a dialysis treatment of a patient to install one or two vascular accesses via which blood moves into the extracorporeal blood circuit and from there back to the patient.

The outer region of the vascular access via which the patient is connected to the machine for carrying out the extracorporeal therapy by means of a needle connection or a hose connection is known as a cause for infections. Viruses, bacteria and germs can move from the surface of the skin into the vascular system of the patient by needle puncturing or the like. This can in particular have negative consequences for patients whose immune defense is reduced. The skin is disinfected around the access area to minimize the risk of introducing viruses, bacteria, germs, etc. into the vascular system of the patient. However, there is typically no check as to whether the disinfection has taken place over the whole area and to a sufficient degree.

It is known from the prior art to determine a sufficient disinfection in that the presence of a disinfectant is checked by means of UV light after is application. Regions that light up are a sign of a sufficient disinfection; dark areas indicate areas of skin to which no disinfectant or only little disinfectant was applied.

It is the underlying object of the present invention to provide a method and an apparatus by means of which it can be simply and reliably determined whether a sufficient disinfection has taken place, in particular of a region of skin of a patient, and whether the risk of infection has thus been reduced.

This object is achieved by the instant invention of (1) a method of disinfecting a region, in particular a skin region of a patient, wherein the method comprises the steps of a) application of an optically effective substance to the region and b) application of a disinfectant to the region, wherein the optically effective substance and the disinfectant are configured such that the optically effective substance is removed from the region by the disinfectant or its optical properties are changed by the disinfectant, as well as by (2) an apparatus for checking the disinfection of a region, in particular a skin region of a patient, wherein the apparatus comprises an emitter for the emission of light onto the region and a detector for detecting the light emanating from the region.

Provision is accordingly made that the method comprises the following steps:
a) Application of an optically effective substance to the region; and
b) Application of a disinfectant to the region, wherein the optically effective substance and the disinfectant are configured such that the optically effective substance is removed from the region by the disinfectant or its properties are changed by the disinfectant. Unlike the known procedure, no check is made in accordance with the invention whether the optically effective substance is present, but rather whether it has been removed or optically changed.

If the optically active substance is removed, this has the substantial advantage with respect to the known method that the optically effective substance cannot enter into the vascular system of the patient by the puncturing by the needle.

In accordance with the invention, the optically effective substance is changed in at least one optical property or is removed by the disinfection, which also includes the case that its concentration and/or quantity on the region or skin is substantially reduced, preferably by at least 75%, in particular by at least 90%, and particularly preferably by at least 99%, with respect to the state before the application of the disinfectant.

The actual disinfection removes or (completely or partly) changes the surface coating of the optically effective substance so that the optical effect has completely or substantially disappeared or has changed after a successful disinfection. This can be detected and so a conclusion can be drawn on whether sufficient disinfection has been carried out or not.

The optically effective substance can, for example, be a means that has fluorescent properties. Skin-compatible fluorine or a skin-compatible substance containing fluorine such as a coumarin compound containing fluorine can be considered, for example.

The term "optically effective" is thus not restricted to the range that is perceivable to the human eye, but rather preferably also or alternatively comprises different wavelength ranges.

The disinfectant is any desired substance that, first, has disinfecting properties and, second, is able to remove the optically active substance or to change its optical properties. Alcohol or an alcoholic solution can be considered as the disinfectant, for example.

It is pointed out at this point that the invention not only covers the actual removal of the optically active substance, but also its change of the optical properties such as the change of the frequency range of the light emitted by the optically effective substance. It can be determined in both cases whether or where the disinfectant was applied.

Light is preferably emitted onto the region in a wavelength range from 350-450 nm, with an optical emission of fluorescent light being emitted in the range from 500-530 nm. These values are only exemplary values which do not restrict the invention.

The region is preferably a skin region of the patient.

In comparison with a procedure in which a fluorescently active substance is mixed in with the disinfectant and a check is then made whether the region in question is sufficiently fluorescent, considerable advantages result due to the procedure that is reversed in accordance with the invention (check of the lack or of the reduction of the optical effectiveness, in particular the fluorescence). The recognizability of individual non-contiguous objects increases significantly when they are arranged illuminated in front of a dark background such as is known from observing the night sky. In contrast, the perceptibility of objects is comparatively small when they are dark objects in front of a bright background. In the dark field, fluorescent surfaces or bright surfaces that are due to deficient disinfection can be recognized better in front of a non-illuminated or dark background than non-fluorescent or non-luminous surfaces in front of a bright background.

In the dark field, i.e. against a dark background, the identification of the disinfection status can be recognized best. A preferred embodiment of the method thus comprises the optically effective substance being selected such that it is perceptible as brighter on an observation or an optical detection than a region that has not been provided with the optically effective substance.

The optical inspection, i.e. the check whether or to what extent the optically effective substance is still present or optically active, preferably takes place by means of an optical measurement device or by a person (quod visio).

In a preferred embodiment of the invention, before the disinfection of the respective skin region or of the region to be disinfected of the patient, its surface is sprayed with fluorine or with a solution containing fluorine and the optical or fluorescent properties are then determined. This measurement or detection serves as a reference measurement.

After a recommended typical disinfection of the skin area or of the region, a further check of the optical or fluorescent properties of the coated region preferably takes place. On a successful disinfection, the coating that has the optically effective substance is completely or largely removed or optically changed by the disinfection.

Regions of emitted light with insufficient disinfection can be liberated from germs, bacteria, viruses, etc. in a repeated disinfection step.

Provision is preferably made that a comparison of the optical properties, e.g. of the fluorescence, is carried out before and after the disinfection and a conclusion is drawn from the comparison on whether the disinfection was sufficient.

Provision is made in a further embodiment that depending on the comparison, that is preferably carried out in an automated manner, it is signaled to the user whether the region has been sufficiently disinfected or whether a repeat disinfection is required.

The process of disinfection preferably comprises two steps. In the first step, the skin area or the region is liberated of germs, dirt and skin particles. In a second step, the skin surface or the region is treated in a virucidal and bacteriacidal manner. A certain residence time of the disinfectant generally has to be observed. In the case of a multi-stage disinfection, the measurement of the optical properties preferably takes place after the last disinfection step.

It must generally be pointed out that the optically effective substance has fluorescent properties. However, any other desired substances are also covered by the invention that have different optical properties that can be detected. The invention is thus not restricted to fluorescence.

The method preferably takes place in an automated or at least partly automated manner. In the case of the automated method, the application of the optically effective substance, the application of the disinfectant, and the (simple or multiple) measurement of the optical properties takes place fully automatically. If a reference measurement and a comparison with the measurement take place after the application of the disinfectant, this comparison and a measurement based on the comparison preferably also take place automatically.

It is conceivable in the case of a partial automation that the application of the optically effective substance and of the disinfectant takes place manually and all the other steps take place in an automated manner.

The present invention preferably does not comprise the step of puncturing the skin, but ends beforehand, i.e. with the disinfection or with the check whether sufficient disinfection has taken place.

The present invention furthermore relates to an apparatus for checking the disinfection of a skin region or of another region of a patient, with the apparatus comprising an emitter for the emission of light onto the skin area or region and a detector for detecting the light emanating from the skin area or region. The apparatus preferably comprises a control unit that activates the emitter and/or the detector at specific points in time.

The emitter can be configured to emit light in a wavelength range from 350-450 nm. The detector can be configured to detect light in a wavelength range from 500-530 nm. They are exemplary values which do not restrict the invention.

The apparatus can have means for applying the optically effective substance and/or means for applying the disinfectant. A fully automatic routine is conceivable such that the apparatus not only carries out the optical measurement, but also the application of the optically effective substance and/or disinfectant, for which corresponding application means are present.

Provision is made in a preferred embodiment that the apparatus has a control unit that activates the emitter and the detector after the application of the optically effective substance and before the application of the disinfectant to carry out a reference measurement and also after the application of the disinfectant.

The apparatus can have a comparator that compares the reference measurement with the measurement after the application of the disinfectant and emits a signal on the basis of the comparison. If a sufficiently large intensity interval results between both measurements, a conclusion can be drawn on a sufficient disinfection.

It is generally also conceivable that the apparatus does not have such a comparator and that no reference measurement is determined, but rather only the optical properties after the application of the disinfectant are determined. In this case, a conclusion can be drawn from the absolute value of the optical properties or from a comparison of this value with a reference value, that can be stored, on whether the disinfection was sufficient or not.

This can be displayed to the user e.g. optically and/or acoustically.

The term of the "optical properties" covers any desired property of the area of skin or of the region of emanating light such as the intensity or brightness, wavelength, color, etc.

The present invention furthermore relates to a blood treatment apparatus, in particular to a dialysis machine, having an apparatus in accordance with the instant invention as described herein. This embodiment of a blood treatment device makes it easy for the operator to recognize whether the access point for the extracorporeal circuit has been sufficiently disinfected (and that the puncturing can therefore be carried out) or whether this is not the case.

Provision is preferably made that the blood treatment apparatus has a power supply for the emitter and/or for the detector and/or storage containers and preferably means for measuring the filling level of the storage containers, with the storage container or containers containing the optically effective substance and/or the disinfectant.

The apparatus or the blood treatment device preferably comprises a storage container for the optically effective substance and/or a storage container for the disinfectant.

The blood treatment device preferably has means that indicate to the user whether the disinfection was sufficient or whether it is necessary to disinfect again.

It is pointed out at this point that the terms "a" and "one" are not necessarily restricted to exactly one of the elements in question, although this is a possible embodiment of the invention. The terms can thus also indicate a plurality of the elements in question. The same applies accordingly to the use of the singular of an element that also comprises the plural and, conversely, to the use of the plural of an element that also comprises only one of the elements.

Further details and advantages of the invention will be described in more detail with reference to an embodiment shown in the drawing.

The drawing shows a skin region 10 of a patient who is to be subjected to a blood treatment by hemodialysis or the skin region of a patient in which the access for a blood treatment takes place.

An optically effective substance S that has fluorescent properties is applied to the skin region 10 before the introduction of the needles forming the vascular access. It can, for example, be a solution that contains a couramin derivative that has at least one fluorine atom.

After the application, the optical properties of this coating are measured and stored. For this purpose, light of a specific, absorbing wavelength (reference numeral 20) is applied to the skin region and the fluorescent light emitted by this skin region is measured by means of a detector 30. This value is stored as a reference value.

A disinfection solution is subsequently sprayed onto this skin region and the optical property of the light that emanates from the skin region is again measured in accordance with the above procedure after a specific residence time. The disinfection solution is configured to remove the optically effective substance from the skin region. A difference from the reference measurement thus results on a repeat measurement of the optical properties.

The apparatus has a comparator that compares the repeat measurement with the reference measurement. If the difference is sufficiently large this is signaled to the user and the puncturing can be carried out. If this is not the case, it is signaled to the user that a repeat disinfection has to be carried out.

The optically effective substance produces regions that appear brighter on the observation by means of the detector 30 than regions that have not had the optically effective substance applied or are no longer applied therewith, which facilitates the recognizability of the removal of the optically effective substance and thus improves the effectiveness of the disinfection.

Instead of the detector 30, the recognition can also be carried out by the human eye, which requires the optical activity or its change to take place in the region of the light perceptible by humans.

The invention claimed is:

1. A method of disinfecting a skin region of a patient, in which access for a blood treatment takes place, wherein the method comprises the following steps:
   a) applying a fluorescent substance to the skin region; and subsequently,
   b) applying a disinfectant to the skin region,
   wherein the fluorescent substance and the disinfectant are configured such that the fluorescent substance is removed from the skin region by the disinfectant or the optical effect of the fluorescent substance completely or substantially disappears by the disinfectant.

2. The method in accordance with claim 1, characterized in that the fluorescent substance is a coumarin derivate containing fluorine.

3. The method in accordance with claim 1, characterized in that the fluorescent substance and/or the disinfectant is/are applied by spraying onto the skin region.

4. The method in accordance with claim 1, characterized in that the fluorescent substance is perceptible as a brighter region on observation or on an optical detection than a region that is not provided with the fluorescent substance.

5. The method in accordance with claim 1, characterized in that optical properties of the applied fluorescent substance are measured after the application of the fluorescent substance and before the application of the disinfectant.

6. The method in accordance with claim 5, characterized in that a comparison of the fluorescent substance optical properties measured before and after a disinfection is carried out and a conclusion is drawn from the comparison on whether the disinfection was sufficient.

* * * * *